United States Patent [19]

Hopkins, II

[11] 4,096,091

[45] Jun. 20, 1978

[54] LIMULUS LYSATE HAVING IMPROVED CAPACITY TO PRECIPITATE IN THE PRESENCE OF LOW ENDOTOXIN CONCENTRATIONS, AND RECONSTITUTING SOLUTIONS THEREFOR

[75] Inventor: Robert E. Hopkins, II, Deerfield, Ill.

[73] Assignee: Baxter Travenol Laboratories, Inc., Deerfield, Ill.

[21] Appl. No.: 489,224

[22] Filed: Jul. 17, 1974

[51] Int. Cl.$^2$ ............ C09K 3/00; G01N 33/16; G01N 31/00; C12K 1/04
[52] U.S. Cl. ............ 252/408; 23/230 B; 195/103.5 R; 424/2; 424/12; 424/95; 424/101; 424/253
[58] Field of Search ............ 252/408; 424/101, 95, 424/253, 2, 12; 23/230 B; 195/103.5 R

[56] References Cited

U.S. PATENT DOCUMENTS 3,954,663   5/1976   Yamamoto et al. ............ 252/408

OTHER PUBLICATIONS

E. Thye Yin, et al., Biochim. Biophys. Acta, vol. 261, pp. 284–289 (1972).
Bryan, F. T., et al., Science, vol. 144, pp. 1147–1148 (29 May 1964).
Chemical Abstracts, vol. 78, No. 95202q (1973).
Chemical Abstracts, vol. 79, No. 89101k (1973).
Young, N. S. et al., J. Clinical Investigation, vol. 51, pp. 1790–1797 (1972).

*Primary Examiner*—Benjamin R. Padgett
*Assistant Examiner*—T. S. Gron
*Attorney, Agent, or Firm*—Paul C. Flattery; John P. Kirby, Jr.; Gary W. McFarron

[57] ABSTRACT

A family of catalysts is disclosed for providing improved capacity for Limulus lysate solution to precipitate in the presence of extremely low concentrations of endotoxin. The catalyst family includes imidazole, manganese ions, Cleland's reagent, magnesium ions, strontium ions, barium ions, cysteine, lithium ions, and various combinations of the above materials. Solutions of the above catalysts may be used to advantage to reconstitute lyophilized Limulus lysate.

46 Claims, No Drawings

LIMULUS LYSATE HAVING IMPROVED CAPACITY TO PRECIPITATE IN THE PRESENCE OF LOW ENDOTOXIN CONCENTRATIONS, AND RECONSTITUTING SOLUTIONS THEREFOR

BACKGROUND OF THE INVENTION

As has frequently been discussed in the published literature, for example, *Thrombos. Diath. Hemorrhage, Vol.* 23, *Pages* 170–181 (1970), the amoebocyte blood cells of members of the genus Limulus, and particularly *Limulus polyphemus,* the horseshoe crab, form clots when placed in contact with pyrogen such as bacterial endotoxin. These amoebocyte cells provide an effective blood clotting mechanism to an injured horseshoe crab, thereby preventing further proliferation and migration of bacteria into other parts of the body.

At the present time, in vivo pyrogen testing of parenteral solutions is performed in rabbits. Such a test program is very expensive and difficult to operate.

A considerable amount of research has been invested in the use of Limulus amoebocytes, after lysing them in water or the like to rupture the cells, as a substitute testing means for pyrogens in sterile products. One typical summary of such recent work with Limulus is found in the *Bulletin of the Parenteral Drug Association, Vol.* 27, *No.* 3, *Pages* 39–148, *May-June,* 1973.

Typically, the Limulus amoebocyte cells are lysed by placing them in distilled water, or by any other convenient means for rupturing the blood cells. Following this, the resulting solution is filtered and centrifuged, to remove solids such as cell wall fragments and the like, to yield a protein solution, commonly referred to as Limulus lysate. This protein solution (Limulus lysate) is conventionally used to detect bacterial endotoxin by bringing it into contact with the material to be tested and observing whether or not a clot of protein is formed which has certain minimum standards of stability.

One typical testing standard for stability of the clot is to invert the test tube in which the clot is formed by 180°. If the clot remains intact, a positive endotoxin reaction is recorded. If the clot breaks up, or no intact clot is ever formed, a negative endotoxin reaction is recorded.

Pure Limulus lysate in sterile water tends to have a lower degree of sensitivity to the presence of endotoxin (no better than 1.56 nanograms of endotoxin per ml.) than the sensitivity of the U.S.P. rabbit test for large volume parenteral solutions (down to 0.097 nanogram of endotoxin per ml.) and thus is usually not suitable for pyrogen testing of such solutions. While certain additives have been previously provided to the Limulus lysate solution to improve the stability of the lysate and the like (*E. Thye Yin, et al., Biochem. Biophys. Acta,* 261 (1972), *Pages* 284–289), there has been no report of the sensitivity of any prior art Limulus lysate becoming equal to that of the U.S.P. rabbit test for large volume parenteral solutions. Calcium has been added as a "potentiator", without achieving the desired sensitivity (*Marchalonis, et al., Journal of Molecular Biology* 32(2), *Pages* 453–465 (1968) ).

In accordance with this invention, various additive materials are disclosed which increase the sensitivity of Limulus lysate, frequently to a level which equals and even can exceed the endotoxin sensitivity which is available by the U.S.P. rabbit test for large volume parenteral solutions. The capacity for Limulus lysate solution to precipitate in the presence of extremely low concentrations of endotoxin is achieved by providing to the solution a catalytic concentration of one or more of the following ingredients: imidazole, manganese ions, Cleland's reagent and other equivalent organic disulfhydryl compounds, strontium ions, barium ions, cysteine and other equivalent organic monosulfhydryl compounds, or lithium ions.

It is generally preferred for the materials specified above to be present in the Limulus lysate solution in the following concentrations, expressed in terms of moles per liter of lysate solution.

| | |
|---|---|
| Imidazole (commercially available from the Eastman Kodak Co.) | 0.004 to 0.4 mole per liter, and preferably 0.01 to 0.3 mole per liter. |
| Manganese | preferably in the $Mn^{++}$ form- 0.005 to 0.1 mole per liter and preferably 0.01 to 0.04 mole per liter. |
| Cleland's reagent (commercially available from Sigma Chemical Co., St. Louis, Missouri) | 0.00005 to 0.0005 mole per liter and preferably 0.0001 to 0.0003 mole per liter. |
| Strontium Ions ($Sr^{++}$) | generally 0.005 to 0.4 mole per liter and preferably 0.01 to 0.3 mole per liter. |
| Barium Ions ($Ba^{++}$) | generally 0.005 to 0.3 mole per liter, and preferably in the presence of well-known "Tris" buffer to provide a pH of 7 to 10. |
| Cysteine | generally 0.005 to 0.3 mole per liter. |
| Lithium Ions ($Li^+$) | generally 0.005 to 0.3 mole per liter and preferably 0.03 to 0.15 mole per liter. |

Magnesium ions by themselves provide excellent sensitization of the Limulus protein if in the presence of no more than 0.1 mole per liter of sodium ions, which tend to act as a suppressant of the catalytic effect of magnesium and generally tend to suppress the sensitivity of the lysate protein to endotoxin, even in the presence of other catalysts. Preferably from 0.05 to 0.3 mole of $Mg^{++}$ ions are present per liter of solution. It is also preferred to avoid the use of hydroxyalkylmines in conjunction with magnesium ions. In the Thye Yin article cited above, "Tris" buffer, which is a hydroxylamine, has been used in combination with magnesium ions in the presence of about 0.15 molar concentration of sodium ions. Both of these materials can suppress the excellent catalytic effect of magnesium ions.

Preferably, the imidazole catalyst of this invention is utilized in the Limulus lysate solution in combination with $Li^+$ ions, $Mg^{++}$ ions, [Thioglycollate]$^-$ ions (which may be added in the form of an alkali metal thioglycollate such as sodium thioglycollate), or $Sr^{++}$ ions. Combinations of these ions with imidazole, which appears to act as a buffering agent, provide a particularly high sensitivity on the part of the Limulus lysate to the presence of endotoxin. For example, in conjunction with the above preferred concentration range of imidazole, excellent and frequently improved results can be obtained by the addition of 0.005 to 0.3 mole of $Li^+$ ions per liter of solution, and preferably from 0.02 to 0.15 mole of the $Li^+$ ions per liter of solution. Similarly, 0.005 to 0.3 mole of $Mg^{++}$ ions, and preferably from 0.01 to 0.1 mole of $Mg^{++}$ ions can be added per liter of solution.

A particularly excellent combination is found when imidazole and $Mg^{++}$ ions are added in their above preferred concentrations, and [thioglycollate]$^-$ ions are likewise added in a concentration of from 0.005 to 0.008 mole per liter of solution. Particularly superior results are usually obtained when from 0.02 to 0.03 mole of $Mg^{++}$ ions; 0.02 to 0.03 mole of imidazole; and 0.001 to 0.002 mole of [thioglycollate]$^-$ ions are present per liter of solution.

Similarly, from 0.001 to 0.01 mole of [thioglycollate]$^-$ ions may be combined with the above concentration ranges of imidazole for improved results. Also, from 0.005 to 0.3 mole of $Sr^{++}$ ions and preferably from 0.02 to 0.15 mole of $Sr^{++}$ ions, per liter of solution, may be added to an imidazole solution to improve the performance over imidazole alone.

The above positively-charged ions may be added to the solution as their respective chlorides, although there has been no experimental evidence to show that the particular anion selected is absolutely critical, except that one should avoid anions which would tend to cause unfavorable side reactions with the Limulus lysate protein, or which render the lithium, magnesium, or strontium cations insoluble, or the like.

The use of the term "catalyst" herein is not intended to imply that the agents of this invention are true catalysts in the precise chemical sense, that is, where catalysts are not considered to be reactants. In this invention, where the mechanism of the action of these "catalysts" on Limulus lysate is not precisely understood, it is possible that the materials or agents disclosed herein as being "catalysts" may also be reactants. Therefore, the terms "catalyst" or "sensitizing agent" are used herein to mean a substance capable of providing improved capacity (or sensitivity) for Limulus lysate solution to precipitate in the presence of extremely low concentrations of endotoxin.

Manganese ions, particularly the $Mn^{++}$ ions, have also been found to be active to potentiate the sensitivity of Limulus lysate. The manganese ions are typically added in the form of manganese chloride, although, as stated above, no particular criticality of the anion has been noted except for the obvious need to avoid insolubilizing anions and those which cause unfavorable side reactions.

Cleland's reagent is a material which is readily commercially available, and which increases the sensitivity of Limulus lysate, particularly when used in the concentrations specified above. It is believed that other organic disulfhydryl compounds will also perform equivalently.

Stontium ions ($Sr^{++}$) give particularly excellent results, particularly when used in the concentrations prescribed above. The chloride of strontium is typically used, but other anions are available as well, subject to the restrictions described above.

Barium ions ($Ba^{++}$) are particularly useful in combination with the well-known and commercially available "Tris" buffer (tris [hydroxymethyl]aminomethane) and equivalent buffering agents, especially when the buffer is present in a concentration to provide a pH of about 7 to 10.

Cysteine, and equivalent sulfhydryl materials (i.e., other organic monosulfhydryl compounds such as glutathione, an alkali metal thioglycollate, or thiouracil) exhibit a capacity to sensitize Limulus lysate, particularly in the concentrations specified above. Satisfactory results have also been obtained when commercially available cysteine hydrochloride is neutralized to about pH 6 to 10 with an alkali material such as sodium hydroxide, potassium carbonate, tetrabutylammonium hydroxide or the like.

In particular, excellent results are obtained by the use in the Limulus lysate solution of 0.02 to 0.2 percent by weight of a sulfhydryl-containing compound such as cysteine or an alkali metal thioglycollate salt, plus from 0.2 to 2 percent by weight of a water soluble magnesium salt such as magnesium chloride. Once again, the anion of the magnesium salt is not seen to be critical, with the exceptions described previously. Sodium thioglycollate is also highly suitable as the sulfhydryl-containing compound.

Lithium ions, such as can be provided by lithium chloride or a similar lithium salt having a soluble, noninterfering anion, are also effective for increasing the sensitivity of the Limulus lysate, particularly when used in the concentrations specified above, and when used in combination with imidazole.

The catalytic or sensitizing agents of this invention are conveniently utilized by first dissolving them in distilled water in the desired concentrations. Thereafter, the resulting solutions can be used to reconstitute lyophilized (freeze-dried) Limulus lysate, by dissolving the Limulus lysate in the solution. This technique is advantageous, because the Limulus lysate is preferably stored in lyophilized condition. The improved Limulus lysate solutions of this invention are preferably prepared immediately prior to use, particularly because their increased sensitivity to endotoxin makes them more likely to precipitate upon the accidental contamination that often takes place over prolonged storage.

As used herein, the term "solution" is primarily intended to refer to a water solution, and typically a distilled, pyrogen-free water solution which avoids premature precipitation of the Limulus lysate. However, it is contemplated that other, non-aqueous solvents such as methanol, ethanol, isopropanol, acetone, ethylene glycol, or other water miscible solvents can be used, particularly in a mixture with water, if desired.

The following examples are offered for illustrative purposes only, and are not to be considered as limiting the invention of this application, which is as defined in the claims below. Weight percentages expressed herein are weight/volume in grams/100 cc.

EXAMPLE 1

Atlantic Ocean horseshoe crabs (*Limulus polyphemus*) were collected and placed in a rack to restrain them in position with their ventral sides facing upwardly. The joint between the first two segments of the crabs (the prosthoma and the opisthoma) was prepared by swabbing with alcohol. The joint was then penetrated with the blood collection needle mounted on the end of a conventional blood bag manufactured by the Fenwal Division of Travenol Laboratories, Inc., Morton Grove, Ill., but modified so that the blood collection tube was only 5 inches in length. The bag contained 300 ml. of 3 percent (weight/volume) sodium chloride solution, containing 2.87 grams of dissolved ethylenediaminetetracetate (EDTA).

The horseshoe crabs were bled one by one as necessary until 300 ml. of blood had passed into the blood bag, which had a 600 ml. capacity. The five-inch blood donor tubing was sealed near its entrance to the bag with a dielectric heat sealer (HEMATRON ® heat sealing unit sold by the Fenwal Division of Travenol Laboratories, Inc.). The blood collection tube was then cut off near the heat-sealed section, to remove the needle.

Two bags, prepared as shown, were selected and balanced as necessary with weights, and then spun in a Sorvall RC3 centrifuge for seven minutes at a 1,000

Gravity force (about 1,800 rpm.), to cause the amoebocyte cells from the Limulus blood to settle. In cases where the blood appears to be sedimenting well, it is sometimes sufficient to only apply a 600 Gravity force (about 1,500 rpm.) for seven minutes.

Following the cell centrifuging step, each blood bag was placed on a 10° inclined plane with the sealed stub of the blood collection tubing pointed downwardly, and the collection tubing was once again opened by cutting. The supernatant was decanted carefully, to leave the settled cells remaining in the bag. Following the decanting step, the collection tubing was once again heat sealed in the manner previously described.

Following this, one of the two sterile access ports (medication ports) of the blood bags was entered with an injection needle, and six parts by weight of distilled, non-pyrogenic water were added for each one part by weight of cells present in the bag, for lysis of the cells. The weight of the cells can be determined conveniently by subtracting the standard dry weight of the blood bag from the actual weight of the specific bag and the cells contained therein.

The distilled water was agitated in the blood bag, and then allowed to stand for 24 hours at 4° C. Following this, the bag was centrifuged at a 1,000 Gravity force for seven minutes.

Following this, the liquid contents of each bag were passed through a 170 micron filter (a sterile Fenwal in line filter set, available from the Fenwal Division of Baxter Laboratories, Inc., Morton Grove, Ill.), to separate them from the settled solids, and placed in a freezing environment until solidly frozen.

The frozen Limulus lysate solution was then carefully thawed, while assuring that the solution remained cold (i.e. below about 20° C). After thawing, the Limulus lysate solution was prefiltered into a pooling bottle through an additional Fenwal 170 micron filter.

The filter residue remaining behind in the filter is unwanted material which has precipitated during the freezing step. The filtrate then is typically filtered once again through another filter (a Millipore type AP25 prefilter having a nominal pore size of 1.5 microns), followed by filtration with a Millipore membrane filter, stated to have an absolute pore size of 1.2 microns, and a nominal pore size of less than that. A nominal pore size is defined as that pore diameter which removes at least 98 percent of all particles of the size stated.

Prior to use, all filters are rinsed with 1 liter of sterile, non-pyrogenic water. The last filtration steps proceed by pressurizing the lysate solution upstream of the filter with approximately 2 lbs. of nitrogen gas pressure. Alternatively, vacuum in the collection vessel can be used to facilitate filtration.

After the last filtering step, the solution is subdivided into 2.0 ml. aliquots, which are placed in 6 ml. vials or test tubes, which have been thoroughly washed with sterile pyrogen-free water, and depyrogenated at 245° C. for 4 hours. The test tubes are then conveniently sealed and shelf-frozen in a lyophilization machine (Virtis Lyophilizer), and allowed to freeze-dry until a dry powder remains.

Reconstitution And Preparation of Limulus Lysate Solution Of Improved Sensitivity A number of the test tubes prepared in the manner described above were each reconstituted as a solution by the addition of 5 ml. of one of the solvents described below.

To calibrate each sample of the Limulus lysate solution so produced, the following tests were performed with respect to each sample.

To each of a series of empty test tubes, excepting the first tube of each series, 0.1 ml. of non-pyrogenic water was added. To the first tube, there was added 0.2 ml. of E. coli standard endotoxin solution (commercially available from Difco Laboratories, Detroit, Michigan). The concentration of the E. coli endotoxin used was 100 nanograms of endotoxin per ml. Following this, 0.1 ml. of solution from the first tube was added to the second tube; and 0.1 ml. of solution for the second tube was added to the third tube; with this process being continued to form a series of successive test solutions, each containing one-half of the concentration of the previous test solutions, so that the twentieth and last test solution contained 0.00019 nanogram of endotoxin per ml.

To each of a selected range of the resulting tubes of solution, there was added 0.1 ml. of a reconstituted lysate solution described below.

The series of tubes were then incubated at 37° C. for 60 minutes. Each tube was then inverted, and the presence or an absence of an intact protein clot was noted. The presence of a protein clot capable of remaining together upon gentle inversion of the test tube was an indication of a positive sensing reaction of the endotoxin by the lysate.

As shown in the table below, the nature of the reconstituting solution significantly affected the endotoxin sensitivity of the lysate. The table shows various of the reconstituting solutions which were tested, and lists for each case the most dilute endotoxin solution that was capable of causing a positive solid clot reaction by the Limulus lysate, after reconstitution in the specific solutions listed below.

For purposes of comparison, the U.S.P. rabbit test for large volume parenteral solutions usually has a detection limit of about 0.097 nanogram of endotoxin per ml. (Solution No. 11).

TABLE I

| Description of Reconstituting Solution Used | Lowest Concentration of Endotoxin Solution Capable of Producing A Positive Solid Clot Reaction (nanograms/ml.) |
|---|---|
| 0.9 weight per cent sodium chloride (control) | 1.56 (Solution No. 7) |
| 0.085 weight per cent L cysteine . HCl | 0.39 (Solution No. 9) |
| 0.1 weight per cent L cysteine | 0.195 (Solution No. 10) |
| 0.001 weight per cent Cleland's reagent. | 0.39 (Solution No. 9) |
| 0.2 weight per cent 2-thio-6-amino uracil | 0.195 (Solution No. 10) |
| An equal volume mixture of 1 weight per cent magnesium chloride solution and 0.085 weight per cent L-cystene . HCl | 0.097 (Solution No. 11) |
| An equal volume solution mixture of 1 weight per cent magnesium chloride solution and 0.1 weight per cent of L-cysteine. | 0.097 (Solution No. 11) |
| An equal volume mixture of 1 weight per cent magnesium chloride solution and 0.1 weight per cent sodium thioglycollate solution. | 0.097 (Solution No. 11) and sometimes 0.048 (Solution No. 12) |
| A 3:2 volume ratio mixture of 1 weight per cent magnesium chloride solution and 0.1 weight per cent sodium thioglycollate solution. | 0.195 (Solution No. 10) |
| A solution mixture of 2 parts by volume of 1 weight per cent magnesium chloride solution; 1 part by volume of 0.9 weight | 0.195 (Solution No. 10) |

TABLE I-continued

| Description of Reconstituting Solution Used | Lowest Concentration of Endotoxin Solution Capable of Producing A Positive Solid Clot Reaction (nanograms/ml.) | |
|---|---|---|
| per cent calcium chloride solution, and 1 part by volume 0.85 weight per cent L-cysteine . HCl. | | |
| An equal volume solution of 1 weight per cent magnesium sulfate solution and 0.2 weight per cent 2-thio-6-amino uracil. | 0.195 | (Solution No. 10) |
| 0.1 weight per cent sodium thioglycollate. | 0.39 | (Solution No. 9) |

EXAMPLE 2

Further samples of a different batch of lyophilized Limulus lysate, prepared as in Example 1, were reconstituted in the manner of Example 1 with 2 ml. of reconstituting solution consisting of 80 volume percent of sterile water and 20 volume percent of 0.13 M imidazole buffer (pH 6.8), and also including additional additives in the concentrations indicated in Table II below:

TABLE II

| Description of Additional Additive in the Reconstituting Solution Used | Lowest Concentration of Endotoxin Solution Capable of Producing A Positive Solid Clot Reaction (nanograms/ml.) | |
|---|---|---|
| Sterile water (control) - no imidazole. | 3.12 1.56 | (Solution No. 6), and sometimes (Solution No. 7) |
| No additive - only imidazole. | 0.195 | (Solution No. 10) |
| Lithium chloride at 0.1 M concentration. | 0.097 0.048 | (Solution No. 11) and sometimes (Solution No. 12) |
| Lithium chloride at 0.05 M concentration. | 0.097 | (Solution No. 11) |
| Lithium chloride at 0.025 M concentration. | 0.097 | (Solution No. 11) |
| Lithium chloride at 0.0125 M concentration. | 0.097 | (Solution No. 11) |
| Magnesium chloride at a concentration of 0.2 M. | 0.097 | (Solution No. 11)* |
| Magnesium chloride at a concentration of 0.1 M. | 0.097 | (Solution No. 11)* |
| Magnesium chloride at a concentration of 0.05 M. | 0.048 | (Solution No. 12) |
| Magnesium chloride at a concentration of 0.025 M. | 0.048 | (Solution No. 12) |
| Magnesium chloride at a concentration of 0.125 M. | 0.048 | (Solution No. 12) |
| Magnesium chloride at a concentration of 0.00625 M. | 0.097 | (Solution No. 11)* |
| Strontium chloride at a concentration of 0.2 M. | 0.097 | (Solution No. 11)** |
| Strontium chloride at a concentration of 0.1 M. | 0.048 | (Solution No. 12)** |
| Strontium chloride at a concentration of 0.05 M. | 0.048 | (Solution No. 12) |
| Strontium chloride at a concentration of 0.025 M. | 0.097 | (Solution No. 11) |
| Strontium chloride at a concentration of 0.0125 M. | 0.048 | (Solution No. 12) |

*Repeat of this experiment on 0.12 M sterile imidazole solution (pH 7.07) resulted in a positive clot reaction at an endotoxin concentration of 0.048 nanogram/ml. (Solution No. 12).

EXAMPLE 3

Further samples of lyophilized Limulus lysate, prepared as in Example 1, were reconstituted in the manner of Example 1 with 2 ml. of reconstituting solution comprising 0.12 M imidazole solution (pH 7.04), and also including additional ingredients in the concentrations indicated in Table III below.

TABLE III

| Description of Additional Ingredients of Reconstituting Solution Used (molar concentration) | Lowest Concentration of Endotoxin Solution Capable of Producing A Positive Solid Clot Reaction (Nanograms/ml.) | |
|---|---|---|
| No additive - only imidazole. | 0.097 | (Solution No. 11) |
| 0.005 M sodium thioglycollate | 0.048 | (Solution No. 12) |
| 0.0025 M sodium thioglycollate | 0.048 | (Solution No. 12) |
| 0.00125 M sodium thioglycollate | 0.048 | (Solution No. 12) |

**Repeat of this experiment in ~0.12 M sterile imidazole solution (pH 7.23) resulted in a positive clot reaction at an endotoxin concentration of 0.025 nanogram/ml. (Solution No. 13).

EXAMPLE 4

Further samples of lyophilized Limulus lysate, prepared as in Example 1, were reconstituted in the manner of Example 1 with 2 ml. of various reconstituting solutions as described below. The endotoxin sensitivity of the resulting products is as shown below:

TABLE IV

| Description of Reconstituting Solution Used | Lowest Concentration of Endotoxin Solution Capable of Producing Positive Solid Clot Reaction (Nanograms/ml.) | |
|---|---|---|
| Sterile Water | A concentration of 0.78 (Solution No. 8) failed to produce a positive reaction | |
| Magnesium chloride at 0.1 M concentration; imidazole at 0.1 M concentration, and sodium thioglycollate at 0.005 M concentration. | 0.195 | (Solution No. 10) |
| Magnesium chloride at 0.05 M concentration; imidazole at 0.05 M concentration; and sodium thioglycollate at 0.0025 M concentration. | 0.097 | (Solution No. 11) |
| Magnesium chloride at 0.025 M concentration; imidazole at 0.025 M concentration; and sodium thioglycollate at 0.00125 M concentration. | 0.048 | (Solution No. 12) |
| Magnesium chloride at 0.0125 M concentration; imidazole at 0.0125 M concentration; and sodium thioglycollate at 0.000625 M concentration. | 0.195 | (Solution No. 10) |
| Magnesium chloride at 0.05 M concentration; lithium chloride at 0.05 M concentration; and imidazole at 0.05 M concentration. | 0.097 | (Solution No. 11) |
| Magnesium chloride at 0.025 M concentration; lithium chloride at 0.025 M concentration; and imidazole at 0.025 M concentration. | 0.097 | (Solution No. 11) |
| Magnesium chloride at 0.1 M concentration; lithium chloride at 0.1 M concentration; imidazole at 0.1 M concentration; and sodium thioglycollate at 0.005 M concentration. | 0.097 | (Solution No. 11) |
| Magnesium chloride at 0.05 M concentration; lithium chloride at 0.05 M concentration; imidazole at 0.05 M concentration; and sodium thioglycollate at 0.0005 M concentration. | 0.097 | (Solution No. 11) |
| Magnesium chloride at 0.025 M concentration; lithium chloride at 0.025 M concentration; imidazole at 0.025 M concentration; and sodium thioglycollate at 0.00125 M concentration. | 0.097 | (Solution No. 11) |
| Lithium chloride at 0.1 M concentration; imidazole at 0.1 M concentration; and sodium thioglycollate at 0.005 M concentration. | 0.097 | (Solution No. 11) |
| Cleland's reagent at 0.0005 M | | |

TABLE IV-continued

| Description of Reconstituting Solution Used | Lowest Concentration of Endotoxin Solution Capable of Producing Positive Solid Clot Reaction (Nanograms/ml.) | |
|---|---|---|
| concentration. | | |
| Cleland's reagent at 0.00025 M concentration. | 0.195 | (Solution No. 10) |
| Cleland's reagent at 0.0000625 M concentration. | 0.097 | (Solution No. 11) |
| Cleland's reagent at a concentration of 0.00025 M; magnesium chloride at a concentration of 0.05 M; and "Tris" buffer at a concentration of 0.00625 M. | 0.195 | (Solution No. 10) |
| Cleland's reagent at a 0.000125 M concentration; "Tris" buffer at a 0.00312 M concentration; and magnesium chloride at a 0.025 M concentration. | 0.097 | (Solution No. 11) |
| Manganous ($Mn^{++}$) chloride at a concentration of 0.05 M. | 0.097 | Solution No. 11 |
| Manganous chloride at a concentration of 0.025 M. | 0.195 | (Solution No. 10) |
| Manganous chloride at a concentration of 0.0125 M. | 0.097 | (Solution No. 11) |
| Manganous chloride at a concentration of 0.00625 M. | 0.097 | (Solution No. 11) |
| Manganous chloride at a concentration of 0.1 M and imidazole at a concentration of 0.125 M. | 0.195 | (Solution No. 10) |
| Manganous chloride at a concentration of 0.00625 M; and imidazole at a concentration of 0.125 M. | 0.097 | (Solution No. 11) |
| Strontium chloride in a concentration of 0.2 M. | 0.097 | (Solution No. 11) |
| Strontium chloride in a concentration of 0.05 M. | 0.097 | (Solution No. 11) |
| Strontium chloride in a concentration of 0.0125 M. | 0.097 | (Solution No. 11) |
| Strontium chloride in a concentration of 0.2 M in "Tris" buffer solution having a pH of 9.3. | 0.048 | (Solution No. 12) |
| Strontium chloride in a concentration of 0.1 M in "Tris" buffer solution of a pH of 9.3. | 0.048 | (Solution No. 12) |
| Strontium chloride in a concentration of 0.0125 M in "Tris" buffer solution with a pH of 9.3. | 0.048 | (Solution No. 12) |
| "Tris" buffer solution control for strontium chloride data (pH 9.3). | 0.39 | (Solution No. 9) |
| Barium chloride in a concentration of 0.2 M. | 0.195 | (Solution No. 10) |
| Barium chloride in a concentration of 0.05 M in "Tris" buffer solution having a pH of 9.55. | 0.097 | (Solution No. 11) |
| Barium chloride of a concentration of 0.025 M in "Tris" buffer solution having a pH of 9.55. | 0.097 | (Solution No. 11) |
| Barium chloride in a concentration of 0.00625 M in "Tris" buffer solution having a pH of 9.5 | 0.195 | (Solution No. 10) |
| "Tris" buffer control for barium chloride data (pH 9.55) | 0.39 | (Solution No. 9) |
| 0.02 M cysteine . HCl, neutralized to pH 7.15 with 5 N sodium hydroxide solution. | 0.195 | (Solution No. 10) |
| Lithium chloride in a concentration of 0.2 M. | 0.195 | (Solution No. 10) |
| Lithium chloride in a concentration of 0.1 M. | 0.097 | (Solution No. 11) |
| Lithium chloride in a concentration of 0.05 M. | 0.097 | (Solution No. 11) |
| Lithium chloride in a concentration of 0.025 M. | 0.195 | (Solution No. 10) |
| Lithium chloride in a concentration of 0.2 M in "Tris" buffer solution of pH 9.55. | 0.097 | (Solution No. 11) |
| Lithium chloride in a concentration of 0.05 M in "Tris" buffer solution of pH 9.55. | 0.097 | (Solution No. 11) |
| Lithium chloride in a concentration of 0.0125 M in "Tris" buffer solution of pH 9.55. | 0.195 | (Solution No. 10) |
| "Tris" buffer solution control for Lithium chloride data (pH 9.55). | 0.39 | (Solution No. 9) |
| Magnesium chloride in a concentration of 0.0125 M in sterile water, and less than 0.1 mole per liter of $Na^+$ ions. | 0.097 | (Solution No. 11) |
| Magnesium chloride in a concentration of 0.05 M in sterile water, and less than 0.1 mole per liter of $Na^+$ ions. | 0.048 | (Solution No. 12) |
| Magnesium chloride in a concentration of 0.2 M in sterile water, and less than 0.1 mole per liter of $Na^+$ ions. | 0.097 | (Solution No. 11) |
| Magnesium chloride in a concentration of 0.05 M in 0.0125 "Tris" buffer solution (pH 8.10), and less than 0.1 M per liter of $Na^+$ ions. | 0.097 | (Solution No. 11) |

That which is claimed is:

1. In a Limulus lysate solution, for providing improved capacity for the solution to precipitate in the presence of extremely low concentrations of endotoxin, the improvement comprising a catalytic concentration of a material selected from the group consisting of imidazole, ionic manganese, Cleland's reagent, glutathione, alkali metal thioglycollates, thiouracil, and cysteine.

2. In a Limulus lysate solution, for providing improved capacity for the solution to precipitate in the presence of extremely low concentrations of endotoxin, the improvement comprising a catalytic concentration of imidazole.

3. The Limulus lysate solution of claim 2 having improved capacity to precipitate in the presence of extremely low concentrations of endotoxin, said lysate solution containing from 0.004 to 0.4 mole of imidazole per liter.

4. The solution of claim 3 in which from 0.01 to 0.3 mole of imidazole are present per liter of solution.

5. The solution of claim 3 in which from 0.005 to 0.3 mole of $Li^+$ ions are present per liter of solution.

6. The solution of claim 4 in which from 0.02 to 0.15 mole of $Li^+$ ions are present per liter of solution.

7. The solution of claim 3 in which from 0.005 to 0.3 mole of $Mg^{++}$ ions are present per liter of solution.

8. The solution of claim 4 in which from 0.01 to 0.1 mole of $Mg^{++}$ ions are present per liter of solution.

9. The solution of claim 3 in which from 0.0005 to 0.008 mole of [thioglycollate]$^-$ ions are present per liter of solution.

10. The solution of claim 9 in which said thioglycollate ions are added to said solution in the form of sodium thioglycollate.

11. The solution of claim 3 in which from 0.005 to 0.3 mole of $Sr^{++}$ ions are present per liter of solution.

12. The solution of claim 4 in which from 0.02 to 0.15 mole of $Sr^{++}$ ions are present per liter of solution.

13. The solution of claim 8 in which from 0.0005 to 0.008 mole of [thioglycollate]$^-$ ions are present per liter of solution.

14. The solution of claim 13 in which from 0.02 to 0.03 mole of $Mg^{++}$ ions; 0.02 to 0.03 mole of imidazole; and 0.001 to 0.002 mole of [thioglycollate]$^-$ ions are present per liter of solution.

15. The solution of claim 14 in which the $Mg^{++}$ ions are added in the form of magnesium chloride.

16. The solution of claim 15 in which said [thioglycollate]$^-$ ions are added in the form of sodium thioglycollate.

17. The solution of claim 3 in which from 0.01 to 0.2 mole of $Li^+$ ions are present per liter of solution.

18. The solution of claim 17 in which said $Li^+$ ions are added in the form of lithium chloride.

19. In a Limulus lysate solution, for providing improved capacity for the solution to precipitate in the presence of extremely low concentrations of endotoxin, the improvement comprising a catalytic concentration of ionic manganese.

20. The Limulus lysate solution of claim 19 having improved capacity to precipitate in the presence of extremely low concentrations of endotoxin, said lysate solution containing from 0.005 to 0.1 mole of ionic manganese per liter.

21. The solution of claim 20 in which from 0.01 to 0.04 mole of $Mn^{++}$ ions are present per liter.

22. The solution of claim 21 in which said $Mn^{++}$ ions are added in the form of manganese chloride.

23. In a Limulus lysate solution, for providing improved capacity for the solution to precipitate in the presence of extremely low concentrations of endotoxin, the improvement comprising a catalytic concentration of Cleland's reagent.

24. The Limulus lysate solution of claim 23 having improved capacity to precipitate in the presence of extremely low concentrations of endotoxin, said lysate solution containing from 0.00005 to 0.0005 mole of Cleland's reagent per liter of solution.

25. The solution of claim 24 in which from 0.0001 to 0.0003 mole of Cleland's reagent are present per liter of solution.

26. In a Limulus lysate solution, for providing improved capacity for the solution to precipitate in the presence of extremely low concentrations of endotoxin, the improvement comprising a catalytic concentration of an organic sulfhydryl-containing compound selected from the group consisting of cysteine, glutathione, alkali metal thioglycollates, and thiouracil.

27. The Limulus lysate solution of claim 26 having improved capacity to precipitate in the presence of extremely low concentrations of endotoxin, said lysate solution containing from 0.005 to 0.03 mole of cysteine per liter.

28. The solution of claim 27 in which said cysteine is added in the form of cysteine hydrochloride neutralized to generally neutral pH with an alkali.

29. The solution of claim 26 which also contains a catalytic amount of magnesium ions.

30. A Limulus lysate solution having improved capacity to precipitate in the presence of extremely low concentrations of endotoxin, said lysate solution containing from 0.2 to 2 percent by weight of water-soluble magnesium salt and from 0.02 to 0.2 percent by weight of an organic sulfhydryl-containing compound selected from the group consisting of cysteine, alkali metal thioglycollate salts, and 2-thioamino uracil.

31. The solution of claim 30 in which said magnesium salt is magnesium chloride.

32. The solution of claim 31 in which said sulfhydryl-containing compound is sodium thioglycollate.

33. An endotoxin-free water solution for reconstituting lyophilized Limulus lysate to produce a solution having improved capacity to precipitate in the presence of extremely low concentrations of endotoxin, said reconstituting solution containing from 0.004 to 0.4 mole of imidazole, and from 0.005 to 0.3 mole of $Mg^{++}$ ions per liter of solution.

34. The reconstituting solution of claim 33 in which from 0.01 to 0.3 mole of imidazole and 0.01 to 0.1 mole of $Mg^{++}$ ions are present per liter of solution.

35. The reconstituting solution of claim 34 in which from 0.0001 to 0.008 mole of [thioglycollate]$^-$ ions are present per liter of solution.

36. The solution of claim 35 in which from 0.2 to 0.15 mole of $Li^+$ ions are present per liter of solution.

37. An endotoxin-free water solution for reconstituting lyophilized Limulus lysate to produce a solution having improved capacity to precipitate in the presence of extremely low concentrations of endotoxin, said reconstituting solution containing from 0.004 to 0.4 mole of imidazole, and from 0.005 to 0.3 mole of $Sr^{++}$ ions.

38. The solution of claim 37 in which from 0.01 to 0.3 mole of imidazole, and from 0.02 to 0.15 mole of $Sr^{++}$ ions are present per liter of solution.

39. An endotoxin-free water solution for reconstituting lyophilized Limulus lysate to provide a Limulus solution having improved capacity to precipitate in the presence of extremely low concentrations of endotoxin, said reconstituting solution comprising from 0.2 to 2 percent by weight of water-soluble magnesium salt and from 0.02 to 0.2 percent by weight of a sulfhydryl-containing compound selected from the group consisting of cysteine, alkali metal thioglycollate salts, and 2-thioamino uracil.

40. The solution of claim 39 in which said magnesium salt is magnesium chloride.

41. The solution of claim 40 in which about 0.5 weight percent of magnesium chloride is present, and about 0.05 weight percent of said sulfhydryl-containing compound is present.

42. The solution of claim 41 in which said sulfhydryl-containing compound is sodium thioglycollate.

43. The solution of claim 41 in which said sulfhydryl-containing compound is cysteine.

44. An endotoxin-free water solution for reconstituting lyophilized Limulus lysate to provide a solution having improved capacity to precipitate in the presence of extremely low concentrations of endotoxin, said reconstituting solution containing from 0.004 to 0.4 mole of imidazole and from 0.005 to 0.3 mole of $Li^+$ ions per liter.

45. The solution of claim 44 in which from 0.03 to 0.15 mole of lithium chloride are present per liter of solution.

46. The solution of claim 32 in which about 0.5 percent by weight of magnesium chloride and about 0.05 percent by weight of sodium thioglycollate is present.

* * * * *

UNITED STATES PATENT AND TRADEMARK OFFICE
CERTIFICATE OF CORRECTION

PATENT NO. : 4,096,091
DATED : June 20, 1978
INVENTOR(S) : Robert E. Hopkins, II It is certified that error appears in the above-identified patent and that said Letters Patent are hereby corrected as shown below:

Column 5, line 67, delete "solvents" and insert therefor --solutions--.

Claim 36, line 1, delete "0.2" and insert therefor -- 0.02 --.

Signed and Sealed this

Twenty-second Day of May 1979

[SEAL]

Attest:

RUTH C. MASON
*Attesting Officer*

DONALD W. BANNER
*Commissioner of Patents and Trademarks*